United States Patent [19]

Northrup et al.

[11] Patent Number: 5,273,716

[45] Date of Patent: Dec. 28, 1993

[54] PH OPTRODE

[75] Inventors: M. Allen Northrup, Berkeley; Kevin C. Langry, Tracy, both of Calif.

[73] Assignee: Electric Power Research Institute, Inc., Palo Alto, Calif.

[21] Appl. No.: 640,484

[22] Filed: Jan. 14, 1991

[51] Int. Cl.$^5$ .............................................. G01N 21/64
[52] U.S. Cl. ............................. 422/82.07; 422/82.08; 436/172; 526/287
[58] Field of Search ............... 422/82.05, 82.06, 82.07, 422/82.08; 436/172, 800, 807; 427/162, 163, 169; 526/287

[56] References Cited

U.S. PATENT DOCUMENTS

| | | | |
|---|---|---|---|
| 4,194,877 | 3/1980 | Peterson | 8/526 |
| 4,476,870 | 10/1984 | Peterson et al. | 128/634 |
| 4,798,738 | 1/1989 | Yafuso et al. | 427/164 |
| 5,114,864 | 5/1992 | Walt | 422/82.07 X |

FOREIGN PATENT DOCUMENTS 0205232 12/1986 European Pat. Off. .

OTHER PUBLICATIONS

Munkholm, C. "Polymer Modification of Fiber Optic Chemical Sensors as a Method of Enhancing Fluroescence Signal for pH Measurement" Analytical Chemistry, vol. 58, pp. 1427-1430 (1986).

Wheaton Manufacturers' Catalogue, Millville, N.J., p. 97, 1989.

Primary Examiner—James C. Housel
Assistant Examiner—Jeffrey R. Snay
Attorney, Agent, or Firm—Heller, Ehrman, White & McAuliffe

[57] ABSTRACT

A process is provided for forming a long-lasting, stable, pH-sensitive dye-acrylamide copolymer useful as a pH-sensitive material for use in an optrode or other device sensitive to pH. An optrode may be made by mechanically attaching the copolymer to a sensing device such as an optical fiber.

8 Claims, 5 Drawing Sheets

PH OPTRODE

BACKGROUND OF THE INVENTION

The present invention is directed to pH optrodes for sensing pH in a liquid environment, and a process for the preparation of such optrodes.

Fiber optic pH sensors have been described in the art using a variety of fluorescent dyes and techniques for immobilizing the dye at the end of the optical fiber. However, there is still a problem with regard to the sensitivity of the fluorescent spaced pH dyes which degrade and can inhibit their long-term usefulness.

U.S. Pat. No. 4,798,738 discloses a method for covalently immobilizing HPTS (hydroxypyrenetrisulfonic acid) dye in a polymer, such as cellulose, on an optical fiber by dissolving the dye-bearing polymer in a solvent and depositing the solvated dye onto the fiber. The dye-bearing polymer is regenerated as a gelatin which coats the tip of the fiber. As a coating, the amount of dye in the polymer at the fiber tip is therefore limited.

It is therefore an object of the present invention to provide pH optrodes in which the amount of fluorescent-sensitive dye seen by the optical sensor is not limited by a coating.

It is a further object of the present invention to provide a pH optrode having improved long-term stability.

It is a further object of the present invention to provide a dye-polymer matrix that is a self-contained structure and can be applied as a sensor in a variety of optical sensing formats.

These and other objects of the invention will be apparent from the following description and from the practice of the invention.

SUMMARY OF THE INVENTION

The present invention provides a process for forming a dye-acrylamide copolymer sensitive to pH in a liquid environment comprising:
(a) covalently linking a pH-sensitive dye containing sulfonate groups through a sulfonamide to acryloyl monomer to form an acryloyl-sulfonamide linkage;
(b) copolymerizing the acryloyl-sulfonamide-containing dye from step (a) with acrylamide monomer to form a dye-acrylamide copolymer.

This dye-acrylamide copolymer can be utilized in a variety of optical sensing formats. The dye-acrylamide copolymer is preferably mechanically immobilized at the end of the optical fiber in a manner such that fluorescence from the dye is detectable at the end of the fiber, such as by containing the fiber in a mesh bag.

BRIEF DESCRIPTION OF THE DRAWINGS

In the accompanying FIG. 1 there is illustrated the preferred procedure for affixing a dye polymer to the end of an optical fiber according to the present invention.

DESCRIPTION OF THE PREFERRED EMBODIMENTS

According to the present invention, a dye-acrylamide copolymer is first formed which will provide the matrix bearing a fluorescent-sensitive dye. As a gel, it can be formed into any desired shape, such as, strips, beads, etc. of any desirable size using conventional techniques. The dye is attached through a sulfonamide group to the acrylamide polymer. The pH sensitive dye may be any sensitive dye containing a sulfonamide group, preferably the dye HPTS, 8-hydroxy-1,3,6-pyrenetrisulfonic acid or any of its salts, preferably its trisodium salt.

In a preferred embodiment, O-acetyl HPTS (having a protected hydroxy group) is used, which is commercially available.

The sulfonate groups are then activated, preferably by treatment with thionyl chloride, to form sulfonyl chlorides. Subsequent treatment with an excess of diamine, preferably 1,6-hexane diamine, forms the corresponding sulfonamides. The terminal (free) amino group on the sulfonamide is reacted with acryloyl chloride. The activated dye is then copolymerized with acrylamide monomer to form the dye-acrylamide copolymer.

It will be realized that other means may be utilized to activate the sulfonate group on the dye to couple it to an acrylamide monomer, for example, other diamines may be utilized to form the sulfonamide The linkage between the sulfonate groups on the dye and the polymer should be through covalent bonds to assure that the dye is irreversibly bound to the polymeric material. The conditions of polymerization of the activated dye with acrylamide monomer are acrylamide polymerization conditions known to those of ordinary skill in the polymerization art.

The ratio of activated dye to acrylamide monomer can be readily adjusted by those of ordinary skill in the art to provide the desired concentration of dye per unit of surface area of a dye-acrylamide copolymer.

The acetyl or other protecting group for the hydroxy group of the dye may be removed by hydrolysis. If acetyl is the protecting group it may be removed, for example, by hydrolysis at a pH of about 10.

Once the dye-acrylamide copolymer is formed it may be shaped into desired shapes or used as is. To modify the pore-size of the copolymer or to increase rigidity, additional cross-linking of the copolymer chains may be accomplished by using cross-linkers.

An appropriate amount of the copolymer bearing the dye will be mechanically affixed to a sensor, such as, at a tip of an optical fiber. This is preferably done by inserting the polymer into a mesh bag at the end of a tube, such as a glass capillary tube, and inserting the end of an optical fiber into the other end of the glass tube and affixing the position of the fiber adjacent to the polymer.

Another preferred method is to confine the copolymer in a tube having a constriction which allows liquid (from the liquid test environment) to pass into the tube without releasing the gel from the tube. The other end of the tube should have an opening of sufficient size to receive the optical fiber which can then be positioned adjacent to the gel.

It will be contemplated that other types of optical sensing configurations may be used, such as slabs or thin films, since the copolymer according to the present invention is a self-contained structure and is mechanically affixed next to the optical sensing device, thus increasing its versatility of application and use.

For an illustrative pH optrode according to the present invention, an acryloyl HPTS monomer was prepared as follows. A 20 mg. sample of O-acetyl-HPTS (Molecular Probes, Inc.) was stirred with 5 ml. of thionyl chloride in 3 drops of DMF at 50° C. for 1.5 hours. The solvent was evaporated under vacuum. The residue was dissolved in methylene chloride, separated from the insoluble material, and the solvent was evaporated. The dye was converted to the sulfonamide by dissolving in dry methylene chloride (3 ml), adding 3 equivalents of diamine (1,6-hexane diamine) and stirring at room temperature for one hour. The product is filtered, solids rinsed with methylene chloride, the filtrate and rinses are combined, and the solvent is evaporated under vacuum. Then 30 microliters of acryloyl chloride and 100 microliters triethylamine were added, the mixture was stirred for one hour, then evaporated to dryness. The resulting acryloyl-HPTS monomer is then polymerized with acrylamide. The O-acetyl group on the dye was removed by hydrolysis at pH 10.

Figure 1:
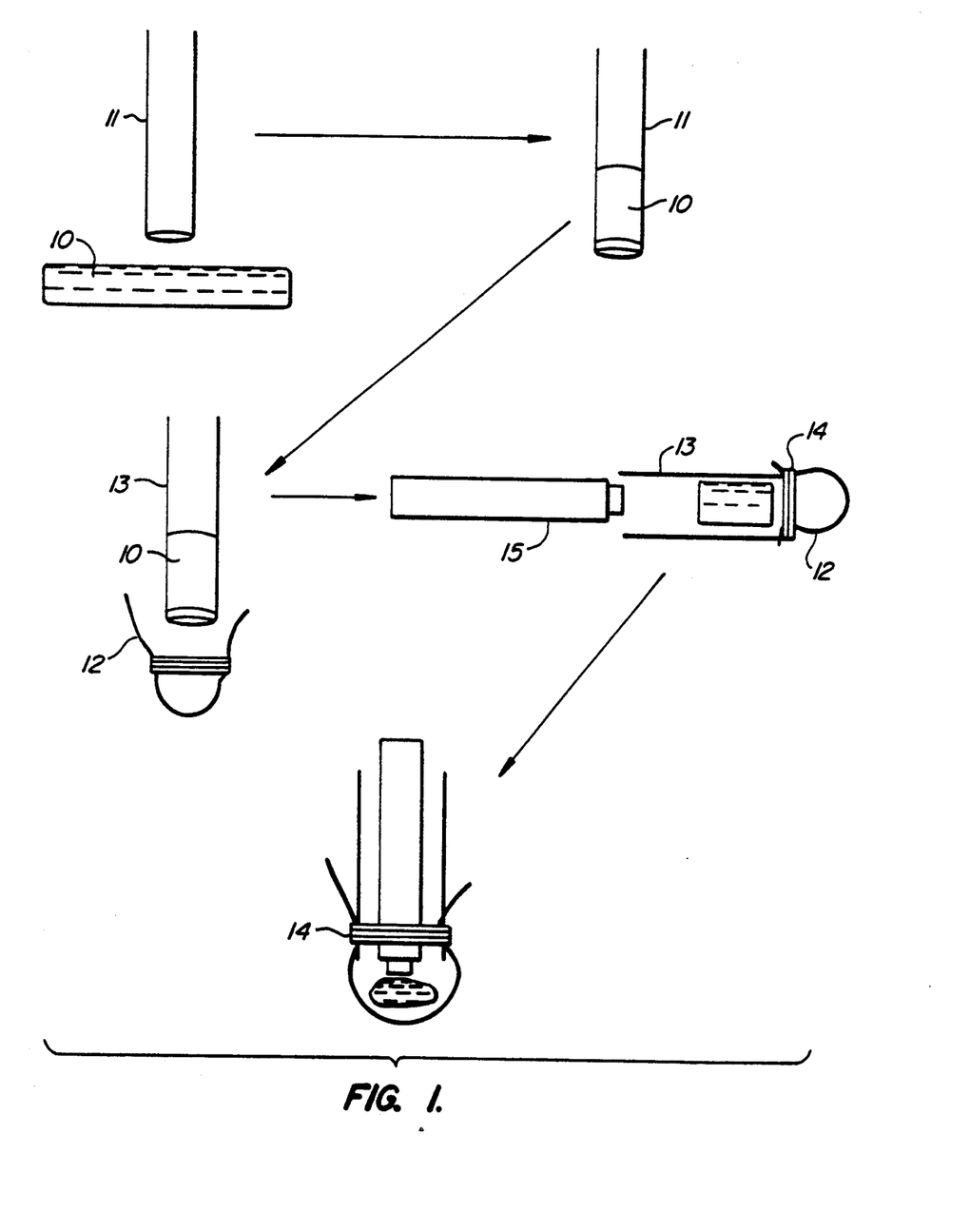

Referring to FIG. 1, strips of the gel 10 are utilized as a sensing means on a pH optrode by attaching a strip 10 to the end of a glass capillary 11. A nylon mesh bag 12 is then wrapped around the end of the capillary 11 bearing the strip 10. The capillary is removed to deposit the strip into the bag 12. The bag 12 bearing the strip 10 is then attached to the end of a glass tube 13 via the attachment band 14 which may be made of any convenient non-corrosive material such as styrene, plastic, and the like. The end of the optical fiber 15 is then placed at the opposite end of the tube 13 and positioned so that the gel is within the detecting range of the tip of the fiber 15. The optical fiber may be then fixed in that position by any appropriate means (not shown) such as by affixing the position of the glass tube 13 onto the optical fiber. To illustrate the invention, the dye-polyacrylamide copolymer was affixed in this manner to the ends of 1000 micrometer optical fibers.

Figure 7:
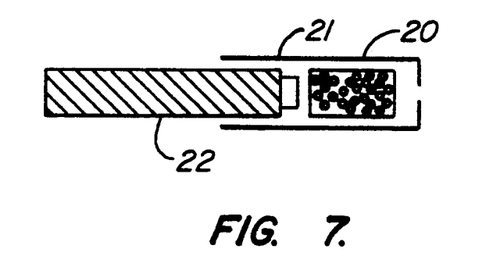
FIG. 7 is an illustration of an alternative embodiment of the present invention.

Referring to FIG. 7, a copolymer strip 20 can be placed in a tube 21 having a constriction at one end which allows ambient liquid to contact the strip. The form and shape of the constriction in tube 21 can be varied to accommodate the desired shape of the copolymer, provided the gel copolymer is maintained within the tube and the shape of the constriction does not prevent the optical fiber 22 from being positioned adjacent to the strip.

A Douglas Instruments Co. Model II Portable Fiber Optic Fluorimeter (Palo Alto, Calif.) was used to measure optrode response. The data reported here was from polymers which had been stored in 100° F. distilled water for one year. Filters were used to provide 405 and 450 nm excitation wavelengths as well as to filter the 530 nm emission signal. The pH buffers were Mallinckrodt and the water soluble HPTS used in the standard HPTS solutions was from Kodak. The pH solutions were confirmed with an Orion Research Model 601A Digital Ionalyzer.

Figure 2:
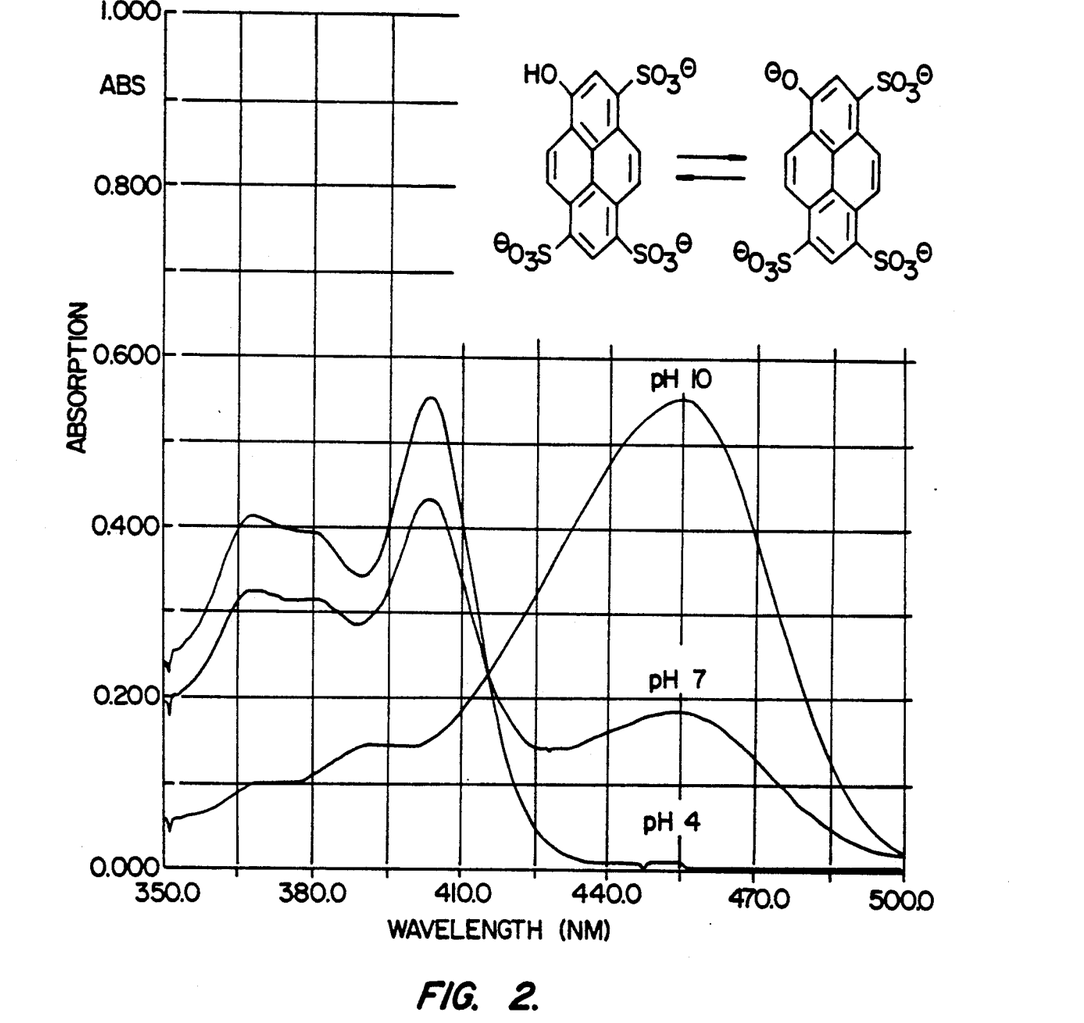
FIG. 2 is a graph of the absorption spectrum of HPTS at pH 4, 7 and 10.

The absorption spectrum of HPTS at pH 4, 7 and 10 is shown in FIG. 2. The emission maximum is centered around 530 nm. The upper right hand corner of FIG. 2 shows the acid and base forms of HPTS. The illumination of HPTS at 450 nm excited a dissociated form of the dye which then fluoresces at 530 nm. Illumination at 405 nm excites the OH form of HPTS to a state that emits around 420 nm. The $pK_a$ of the ground state dissociation is around 7.2 while that of the excited state reaction is about 1.4. Therefore, the single emission wavelength at 530 nm can be monitored, while changing the excitation wavelength between 405 and 450 nm V. The pH of the sample solution is then correlated to the ratio of the two measurements.

Figure 3:
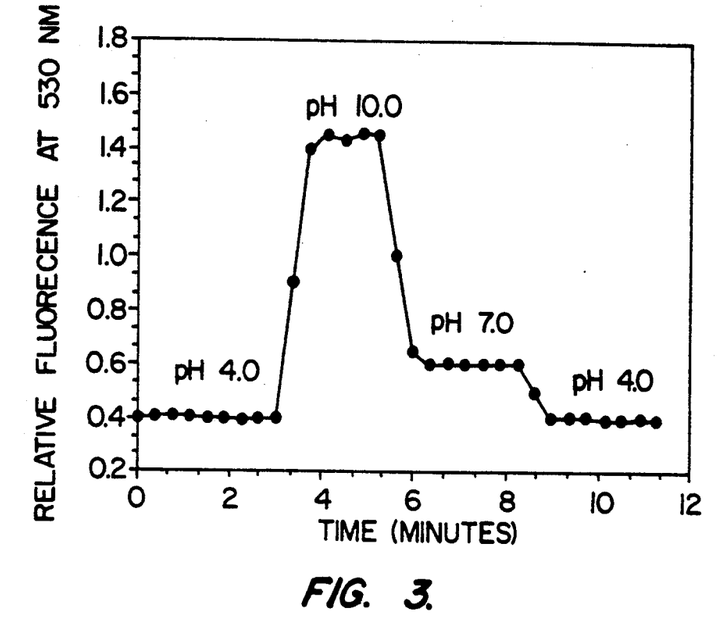
FIG. 3 is a graph of a response curve of an optrode according to the present invention using 450 nm excitation.

FIG. 3 shows a typical response curve for an optrode from pH 4, 7 and 10 using 450 nm excitation. All data for FIGS. 3–6 was taken on dye gels made according to the invention which had been stored for one-year at 100° F. in distilled water. The water was periodically changed during storage. Response time for a pH change of 4 to 10 is about one minute. The response time may be modified by changing the amount of polymer placed in the optrode. Diffusion within the polymer and not the nylon filter appears to be the major limiting factor for the response of the optrode.

Figure 4:
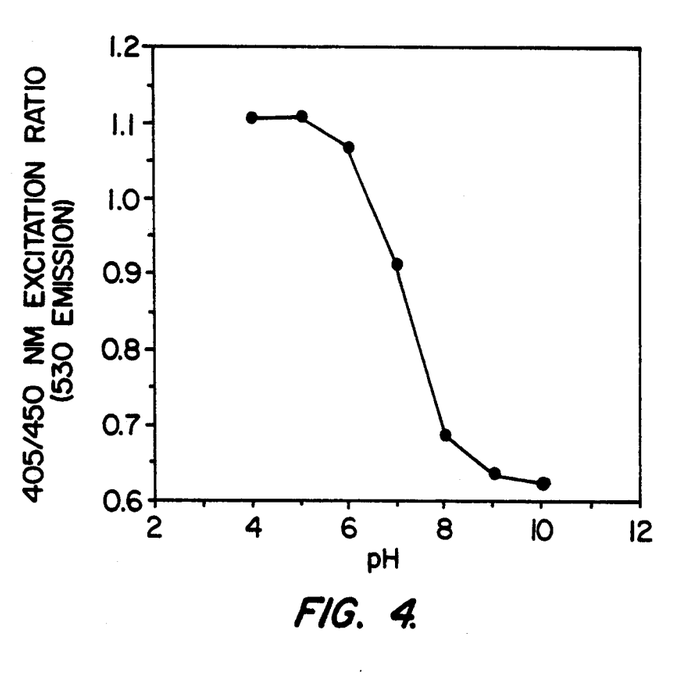
FIG. 4 is a graph showing the ratiometric response of an optrode according to the invention at pH 4–10.
Figure 5:
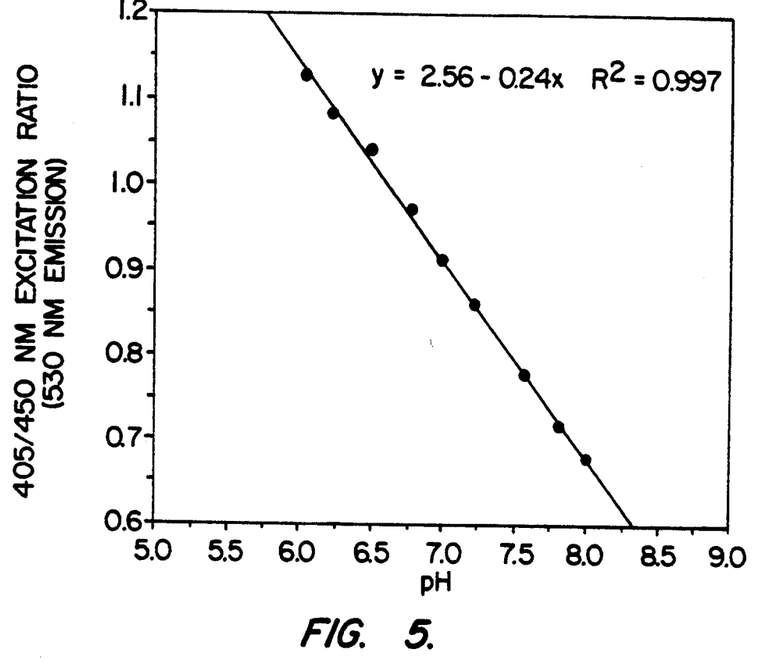
FIG. 5 is a graph of optrode response to solutions of pH 6 through 8.
Figure 6:
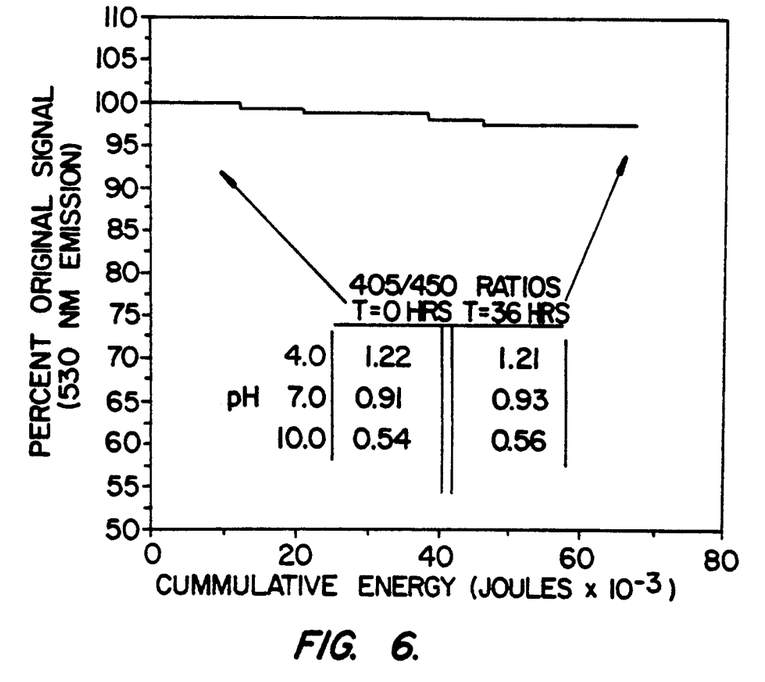
FIG. 6 is a graph of a photodegradation study of an optrode of the invention.

The optrode ratiometric response (405 nm excitation/450 nm excitation) from pH 4 through 10 is shown in FIG. 4. This sigmoid-shaped curve presents the expected near-linear range for HPTS between pH 6 and 8. FIG. 5 shows the optrode's response to solutions of pH 6 through 8. Data was taken at 0.25 pH unit intervals.

To test the photostability of the optrode, a photodegradation study was performed. These results are presented in FIG. 6. This figure demonstrates the effect of constant illumination at 450 nm of the optrode for a period of over 36 hours at pH 7. The light output at the fiber tip at this wavelength was approximately 500 nanowatts. These results demonstrate the photostability of the seasoned optrode (loss of less than 2.5 percent of signal over the approximate equivalent of 4500 duty cycles of 30 s each). The table within the graph shows that the 405/450 nm excitation ratios did not change significantly between the beginning and the end of this photo-stability experiment.

What is claimed is:

1. A method for forming a pH-sensitive optrode comprising the steps of:
   (a) covalently linking hydroxypyrenetrisulfonic acid, or its salts, having sulfonate groups to an acyloyl monomer through sulfonamide linkages formed by activating and reacting said sulfonate groups with at least three equivalents of a diamine to form sulfonamide groups, said sulfonamide groups reacting with said acryloyl monomer to form acryloyl-hydroxypyrenetrisulfonic monomer; and
   (b) copolymerizing said acryloyl-hydroxypyrenetrisulfonic monomer from step (a) with acrylamide monomer to form a dye-acrylamide copolymer, said dye being linked by covalent bonds to form a dye-polymer matrix; and
   (c) shaping said dye-acrylamide copolymer to form a self-contained structure and immobilizing said dye-acrylamide copolymer near the end of an optical fiber so that fluorescence from said dye is detectable via said optical fiber.

2. A method according to claim 1 wherein said step (c) comprises attaching a mesh bag containing said dye acrylamide copolymer to one end of a tube, inserting one end of said optical fiber into the other end of said tube and affixing the position of said optical fiber in said tube adjacent to said dye-acrylamide copolymer.

3. A pH-sensitive optrode formed by the method set forth in claim 2.

4. A method according to claim 1 wherein said step (c) comprises confining said dye-acrylamide copolymer in a tube having a constriction at one end which allows liquid to pass into said tube without releasing said dye-acrylamide copolymer from said constricted end of said tube, and inserting said optical fiber into a second end of said tube and affixing the position of said optical fiber in said tube adjacent to said dye-acrylamide copolymer.

5. A ph-sensitive optrode formed by the method set forth in claim 4.

6. A process for forming a dye-acrylamide copolymer sensitive to pH comprising:
(a) covalently linking hydroxypyrenetrisulfonic acid, or its salts, having sulfonate groups to an acryloyl monomer through sulfonamide linkages formed by activating and reacting said sulfonate groups with at least three equivalents of a diamine to form sulfonamide groups, said sulfonamide groups reacting with said acryloyl monomer to form acryloyl-hydroxypyrenetrisulfonic monomer; and
(b) copolymerizing said acryloyl-hydroxypyrenetrisulfonic monomer from step (a) with acrylamide monomer to form said dye-acrylamide copolymer, said dye being linked by covalent bonds to form a dye-polymer matrix.

7. A pH-sensitive dye-acrylamide copolymer formed by the process set forth in claim 6.

8. A method according to claim 6 or 1 wherein said acryloyl monomer comprises acryloyl chloride.

* * * * *

UNITED STATES PATENT AND TRADEMARK OFFICE
CERTIFICATE OF CORRECTION

PATENT NO. : 5,273,716

DATED : December 28, 1993

INVENTOR(S) : M. ALLEN, KEVIN C. LANGRY

It is certified that error appears in the above-indentified patent and that said Letters Patent is hereby corrected as shown below:

Column 4, line 8, "V" should be deleted;

Column 4, line 46, "acyloyl" should be --acryloyl --; and

UNITED STATES PATENT AND TRADEMARK OFFICE
CERTIFICATE OF CORRECTION

PATENT NO. : 5,273,716
DATED : December 28, 1993
INVENTOR(S) : M. ALLEN, KEVIN C. LANGRY Page 2 of 2

It is certified that error appears in the above-indentified patent and that said Letters Patent is hereby corrected as shown below:

In the drawings, Sheet 5, Figure 7, the line from reference 20 should be extended to connect with the copolymer strip as shown below:

FIG. 7.

Signed and Sealed this

Sixth Day of September, 1994

Attest:

BRUCE LEHMAN

Attesting Officer

Commissioner of Patents and Trademarks